(12) United States Patent
Lechner-Fish et al.

(10) Patent No.: US 6,536,471 B2
(45) Date of Patent: Mar. 25, 2003

(54) LOW-COST STREAM SWITCHING SYSTEM

(75) Inventors: Teresa Lechner-Fish, Katy, TX (US); Henry Mancha, Houston, TX (US)

(73) Assignee: Daniel Industries, Inc., Houston, TX (US)

( * ) Notice: Subject to any disclaimer, the term of this patent is extended or adjusted under 35 U.S.C. 154(b) by 0 days.

(21) Appl. No.: 09/901,784

(22) Filed: Jul. 9, 2001

(65) Prior Publication Data

US 2003/0005964 A1 Jan. 9, 2003

(51) Int. Cl.[7] .............................................. F16K 11/10
(52) U.S. Cl. ...................................... 137/597; 137/371
(58) Field of Search ................................ 137/597, 341

(56) References Cited

U.S. PATENT DOCUMENTS

| | | | | |
|---|---|---|---|---|
| 5,325,889 A | * | 7/1994 | Paul et al. | 137/594 |
| 5,368,062 A | * | 11/1994 | Okumura et al. | 137/240 |
| 5,765,591 A | * | 6/1998 | Wasson et al. | 137/597 |
| 6,363,966 B1 | * | 4/2002 | Browne | 137/597 |

* cited by examiner

*Primary Examiner*—Stephen M. Hepperle
(74) *Attorney, Agent, or Firm*—Conley Rose, P.C.

(57) ABSTRACT

A novel stream switching system includes a unitary housing having a common stream path for a multitude of fluid streams from, for example, a process pipeline. A set of solenoids or other switches attached to the housing directly controls the flow of each fluid stream. Preferably, the solenoids are default-closed, low dead-volume solenoids that, unlike conventional low dead volume solenoids, are closed if not supplied with electricity. These solenoids are adapted to the wide temperature ranges encountered in the pipeline environment by increasing the voltage applied to the solenoids. The housing also preferably includes a pre-heat region to warm the sample to a desired temperature.

15 Claims, 10 Drawing Sheets

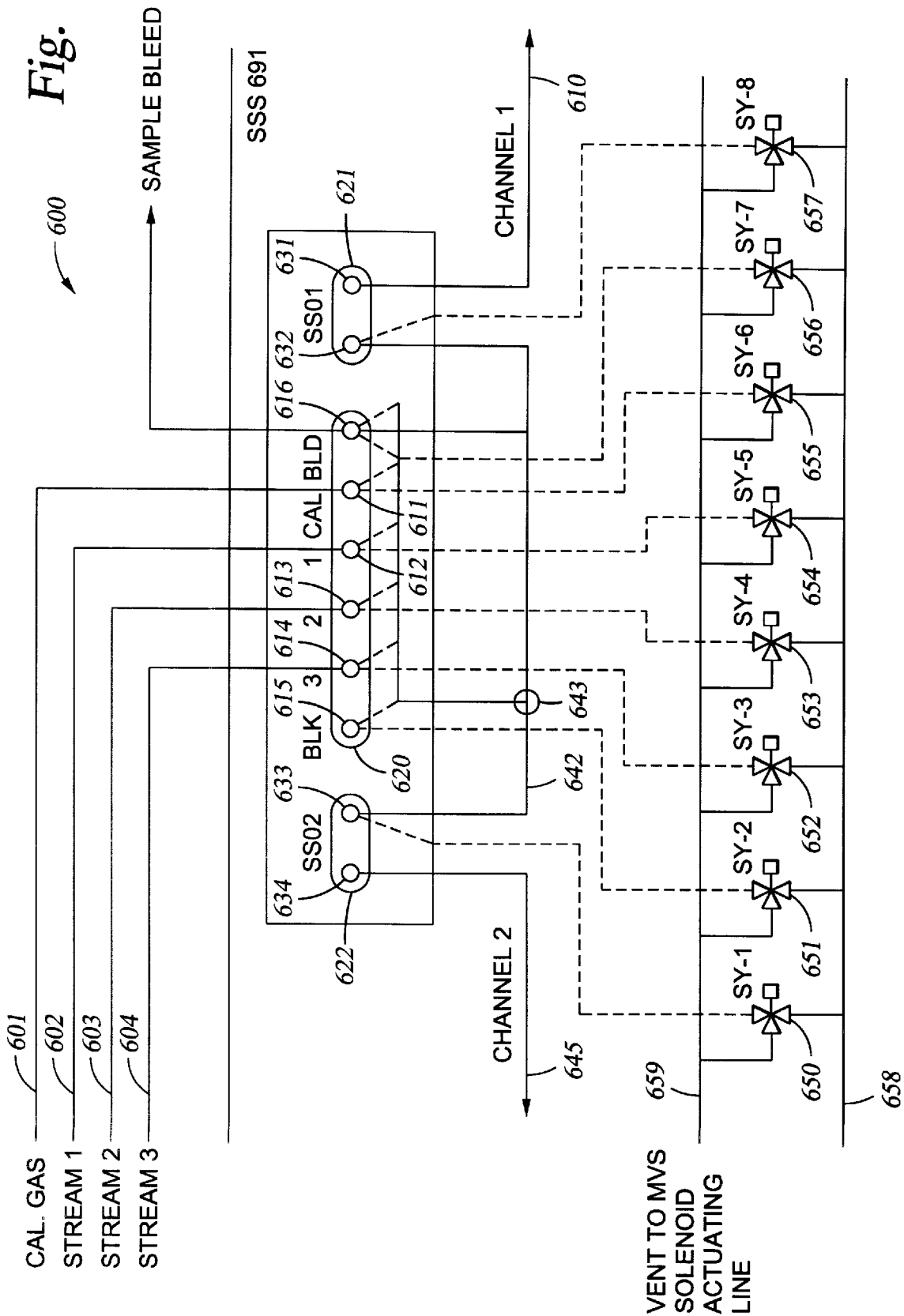

LOW-COST STREAM SWITCHING SYSTEM

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

The invention relates to a sampling system. Preferably, the invention relates to a stream switching system for fluid analysis.

2. Description of the Related Art

It is often very important to know what fluids are flowing through a conduit such as a pipeline. For example, a buyer and seller of gas may agree upon a price for the fluid flowing through a process pipeline based upon the content of the fluid stream. Thus, the fluid content must be measured. Where multiple pipelines are positioned near one another, it may be economical to use a single meter or measurement device to monitor all of the fluid flows. The device used to extract and deliver the fluid to the measurement device is traditionally referred to as a sampling system. The sampling system provides fluid sample to a measurement device such as a gas chromatograph.

FIG. 6 shows a "double block and double bleed" stream switching system for selectively supplying various fluid samples to downstream devices such as sample valves. The stream switching system 600 includes four streams 601–604 upstream of a stream-handling portion 691. The four streams include a calibration sample 601, stream 1 602 corresponding to a first fluid sample, stream 2 603 corresponding to a second fluid sample, and stream 3 604 corresponding to a third fluid sample.

Streams 601–604 supply various fluid samples and connect respectively to actuatable calibration port 611 and actuatable stream ports 612–614. Actuatable ports 615–616 and 632–633, as well as ports 631 and 634, are also part of the sample-handling portion 691. Each actuatable port may be actuated into either an open or closed state as controlled by eight connected solenoids 650–657 (also labeled SV1–SV8) which correspond respectively to ports 611–616, 632–633. When a port is in an open state, fluid may pass freely through the port. When a port is in a closed state, fluid is prevented from flowing through that port. Also shown in FIG. 6 are solenoid pressure line 658 and solenoid vent line 659, as well as gas path 642 extending from port 615 to ports 633 and 632.

Each actuatable stream port 612–614, as well as actuatable calibration port 611, is positioned in an area 620 that creates a common sample path. Also positioned in the common sample path 620 are an actuatable "blocking" port 615 and an actuatable "bleed" port 616. In addition, area 621 creates a first sample shut off that contains two "blocking" ports 632 and port 631. Area 622 creates a second sample shut off that contains two "blocking" ports 633 and port 634. As shown, ports 632 and 633 are actuatable, while ports 631 and 634 are not.

Two channels, channel 1 640 and channel 2 645, are output tubing that direct fluid sample away from the stream switching system. The channels connect to, for example, downstream gas chromatographs including valve, heating, and measurement devices. Each channel thus may be separately analyzed by a gas chromatograph. Each channel can also be used as a flow path to "bleed" the system when switching from sample point to sample point.

As can also be appreciated, first and second sample shut offs correspond to first and second channels 640, 645. Consequently each channel is associated with two solenoids 650 and 657, either one of which can be actuated to prevent the flow of any fluid through the channel. In the illustration, the flow of fluid through channel 1 may be prevented by closing either actuatable blocking port 615 or actuatable port 632 in the first sample shut off. Similarly, the flow of fluid through channel 2 may be prevented by closing either actuatable blocking port 615 or the actuatable port 633 in the second sample shut off. Thus, because the flow of fluid may be prevented through a channel at either of two locations, this is a "double block" design. In addition, the system may be bled through sample bleed port 616. Thus, because the system may be bled either through a channel or through the sample bleed port 616 the embodiment is a "double bleed" design.

Referring now to FIG. 7, a side exploded view of the stream switching portion 691 is shown. The stream switching portion constitutes upper, middle, and lower plates aligned and connected together by dowel pins 770 and torque screws 771–775. The lower plate, referred to as a manifold plate 710, includes eight actuation ports 711–718 connected by tubing to solenoids 650–657 (not explicitly shown in FIG. 7). The middle plate, also called a piston plate 720, includes eight locations 721–728 designed to receive respective pistons 750–757. Middle plate 720 also includes shallow channels, chambers, or grooves that form areas 620–622, as described with reference to FIG. 6. The upper plate, referred to as the primary plate 730, includes screw holes corresponding to the torque screws, as well as three exemplary fluid ports 616, 632, and 631. Eight pistons 750–757 (corresponding to ports 611–616, 632–633) as well as a pair of actuating diaphragms 740 lie between manifold plate 710 and middle plate 720. Sealing diaphragm 765 and cushion diaphragm 760 lie between the primary plate 730 and middle plate 720. The sealing and actuating diaphragms may be made from KAPTON polyimide film.

Each solenoid is placed in a closed position by the application of actuation gas from connected tubing. The application of the actuation gas for each individual solenoid is, in turn, controlled by a processor and associated software.

Although this stream switching system has significant advantages over previous designs, the use of actuating diaphragms, plates, and numerous pistons makes the system more expensive than is desirable. In addition, in the unlikely event that the electrical power to the solenoids is turned off and the carrier gas stream fails, sample leaks through the system. Although such a circumstance is uncommon, any leakage of the sample is undesirable.

A stream sampling system is needed that is less expensive than those previously in existence. This stream sampling system should be more resistant to operational failure than previous stream sampling systems is needed. Ideally, such a novel system could be compatible with the processor and software used with previous systems to enable single substitution of the novel system for the old.

SUMMARY OF THE INVENTION

One embodiment of the invention features a housing with an exterior, and a common stream path with connected first port, second port, and third port. Flow switches connect to the three ports and to three fluid sources, each flow switch being actuatable between an open position that allows flow of fluid from said the corresponding fluid source through said flow switch and a closed position that prevents the flow of fluid from the fluid source. Advantageously, each switch is in a closed position in the absence of electrical power applied to the switch.

Tubing is attached to the housing and may connect the common stream path to additional stream shut off solenoids. The housing is preferably a one-piece housing made from stainless steel. It also preferably includes a heating channel for warming fluid sample to a desired temperature.

Thus, the, present invention comprises a combination of features and advantages that enable it to overcome various problems of prior devices. The various characteristics described above, as well as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiment of the present invention, reference will now be made to the accompanying drawings, wherein:

FIG. 6 is a schematic of an earlier design of a stream switching system;

DETAILED DESCRIPTION OF THE PREFERRED EMBODIMENT

Figure 1A:
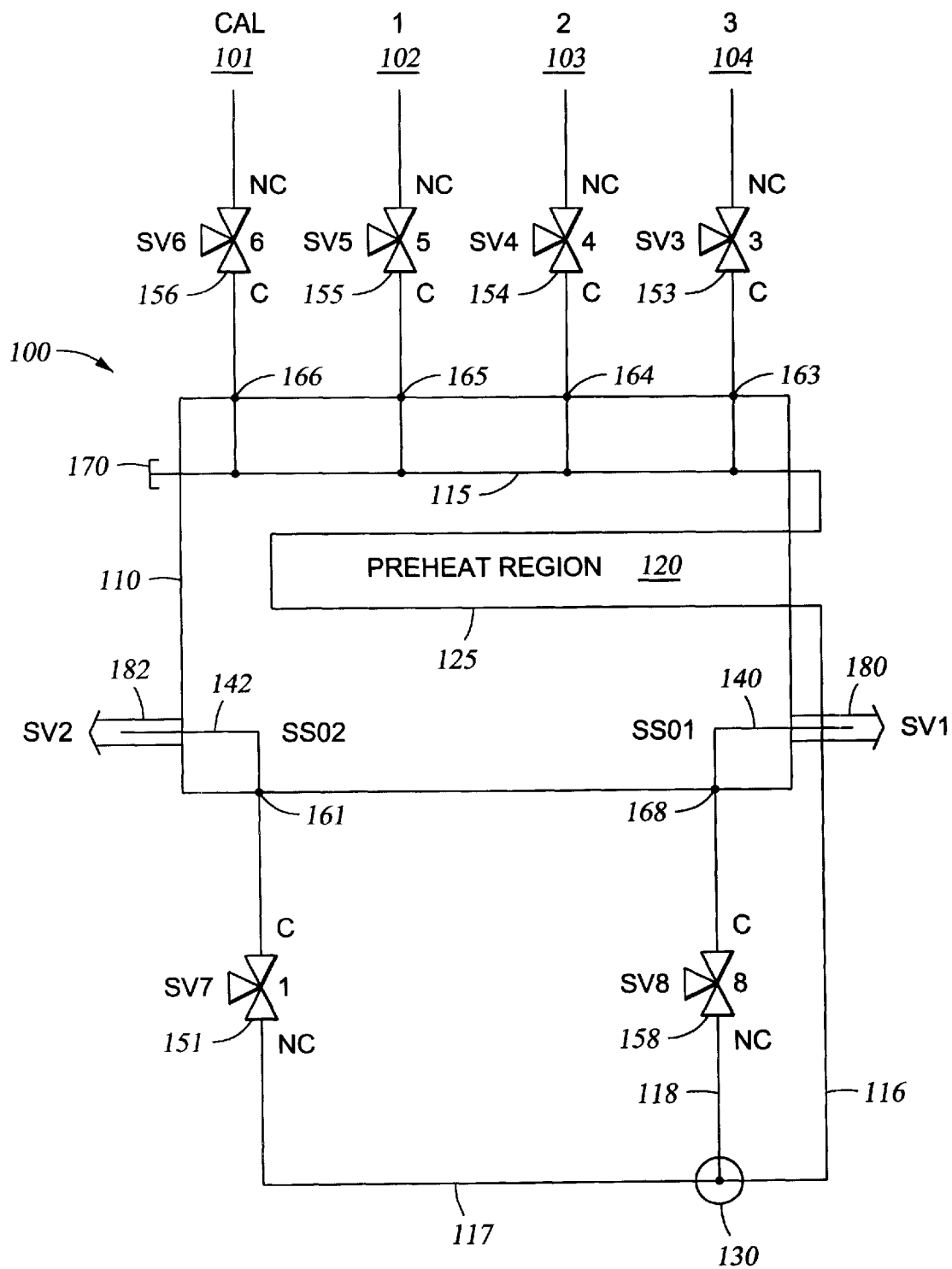
FIG. 1A is a schematic of a first embodiment of the invention.
Figure 1B:
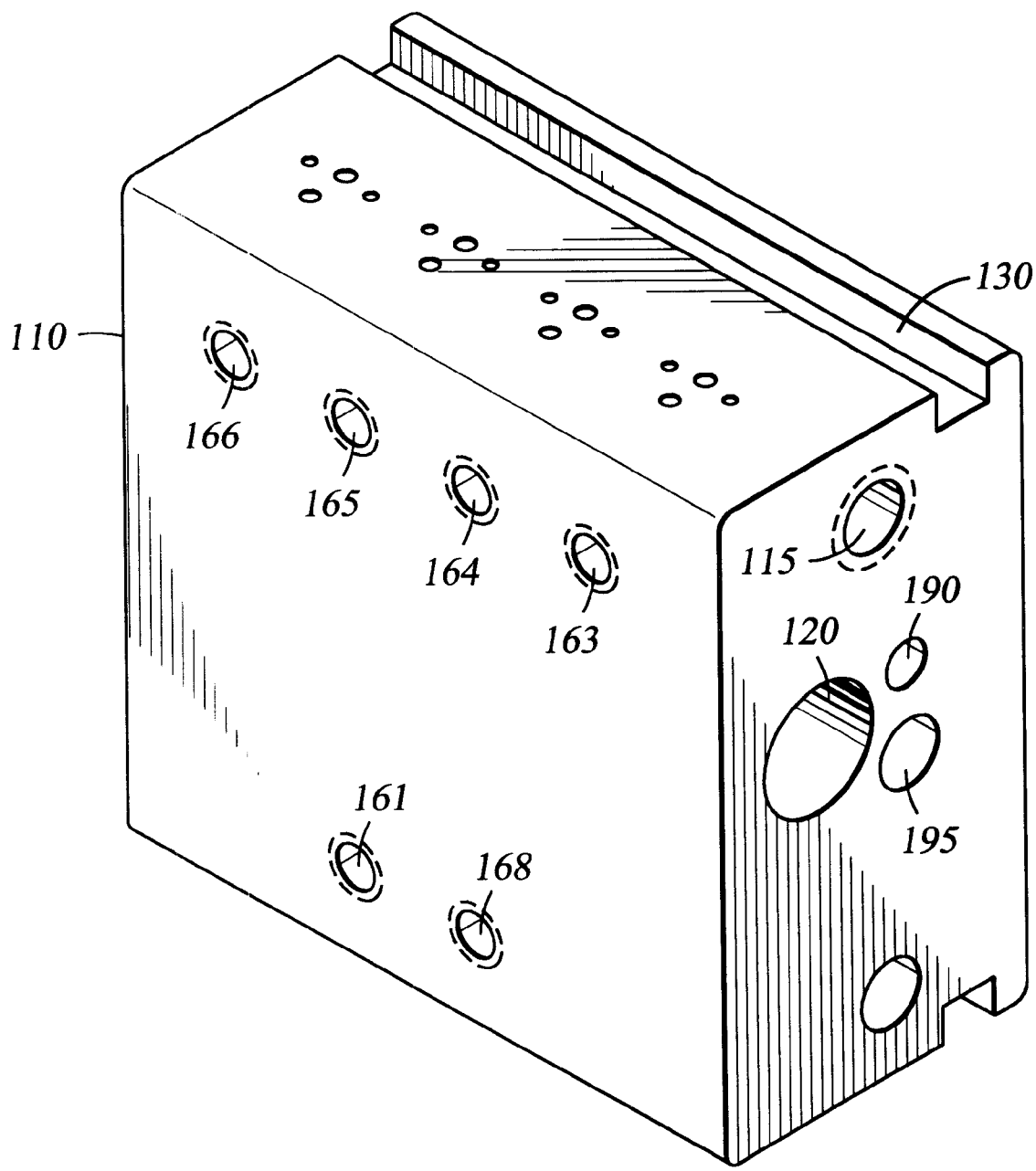
FIG. 1B is a perspective view of a housing for the embodiment of FIG. 1.

FIG. 1A shows a schematic of a first embodiment of a novel stream switching system. Stream switching system 100 includes a housing 110 (a perspective view of which is shown in FIG. 1B) with gas ports 161, 163–166, 168. Calibration and sample streams 101–104 connect to ports 163–166. Housing 110 forms a common path channel 115 and a pre-heat region 120. Tubing 116 connects to housing 110 from the pre-heat region 120 to continue the common stream path. As used with reference to the invention, the term tubing is used in a general manner and includes other fluid transportation mediums such as piping. A plug 170 may be inserted in housing 110 at one end of common path channel 115. A plurality of solenoids 151, 153–156, 158 attach to ports 161, 163–166, 168. A union tee flow splitter 130 attaches upstream to channel 116 and downstream to channels 117 and 118. Sample shut off channel one ("SS01") 140, and sample shut off channel two ("SS02") 142 attach to solenoids 151 and 158, respectively, by ports 161 and 168. Two TEFLON fluoropolymer film sleeves 180, 182 communicate with SS01 140 and SS02 142, respectively, and connect to one or more downstream gas chromatographs or sample valves (not shown). Tubing connects to common path channel 115 and acts as a pre-heat coil while inserted in pre-heat region 120. An optional restrictor 125 such as capillary tubing may also be present, if desired. An associated processor and software (not shown) control the opening and closing of each solenoid.

FIG. 1B shows a unitary housing 110 for the system of FIG. 1A. Although it is to be understood that housing 110 could be constructed from multiple pieces, it is preferred that housing 110 be a one-piece housing made from stainless steel. Such a construction is desirable because it is conductive to heat, resistant to breakage, highly leak resistant, and shows only small variances during manufacture from housing to housing. Elements corresponding to those in FIG. 1A are so labeled. Notable is channel 130, which provides heat dissipation for the solenoids. Also shown are ports 190 and 195 for insertion of a suitable heater and a thermal detector such as the well-known RTD. A suitable heater might be a 10-watt cartridge heater at 12 volts or, possibly, a 10-watt cartridge heater at 24 volts.

During operation, the stream switching system 100 from FIG. 1A provides sample from any of three sample streams (or calibration stream) 101–104 to either or both of SS01 channel 140 and SS02 channel 142. For example, it may be desirable to provide a sample from sample stream 1 to a downstream sample valve SV1. The solenoid attached to stream 1, solenoid 155, is turned open to allow sample to flow. Solenoids 153, 154, and 156 are in a closed position, preventing the flow of fluid through these solenoids. It can be appreciated that the use of a solenoid in particular to prevent the flow of fluid is not absolutely necessary, and any suitable mechanical or electrical gas flow actuation switch may be used. However, as explained below, the preferred solenoids are especially adapted to improve the performance of the stream switching system over a wide range of temperatures and to resist system failure from a lack of power. Downstream, at least one of solenoids 151 or 158 are also turned open to allow fluid to flow. Sample from sample stream 1 then travels through solenoid 155, through union tee flow splitter 130 to either or both of solenoids 151, 158, and then downstream to sample valve 1 (SV1) or sample valve 2 (SV2) for analysis. It should be appreciated that other geometries of splitters could be employed and remain within the scope of the invention. The illustrated union tee flow splitter is both simple and efficient, however.

It is notable that the union tee flow splitter is mounted against the housing 110 in an inverted, horizontal position. All other factors being the same, a horizontal placement (i.e. the long portion or the top of the union tee being in the horizontal plane) of the flow splitter helps achieve a 50/50 flow from the common line to the separate lines leading to each of the sample shut offs. If the union tee were oriented so that the common line entered the long portion of the union tee, the heavier molecules in the sample may preferentially continue in a straight path. This discrimination would lead to different sample compositions being transported to sample shut off channel one and sample shut off channel two.

After the sample is downstream of a sample shut off channel (SS0), the respective solenoid (151 or 158) is placed in a closed position and the sample is allowed to equibrilate with atmospheric pressure, which improves measurement accuracy. Because any particular sample travels through two solenoids in the system, the embodiment of FIGS. 1A and 1B is a "double block" system.

During this process, the sample is heated to a selected temperature by housing 110 while the sample flows through the pre-heat region 120 of the common path channel 115. Housing 110 is heated by a heating element. Insulative housing (not shown) may surround housing 110 to help maintain a constant housing temperature. Tubing comprises the common path channel through the pre-heat region 120, and the tubing is coiled in a manner well known to those of ordinary skill in the art to assist in the heating of the sample. Restrictor 125, which may be capillary tubing or any other suitable restrictor, may be included to slow sample fluid flow velocity and thereby lengthen the amount of time spent by the sample in pre-heat region 120. This, in turn, improves heating of the sample.

Figure 7:
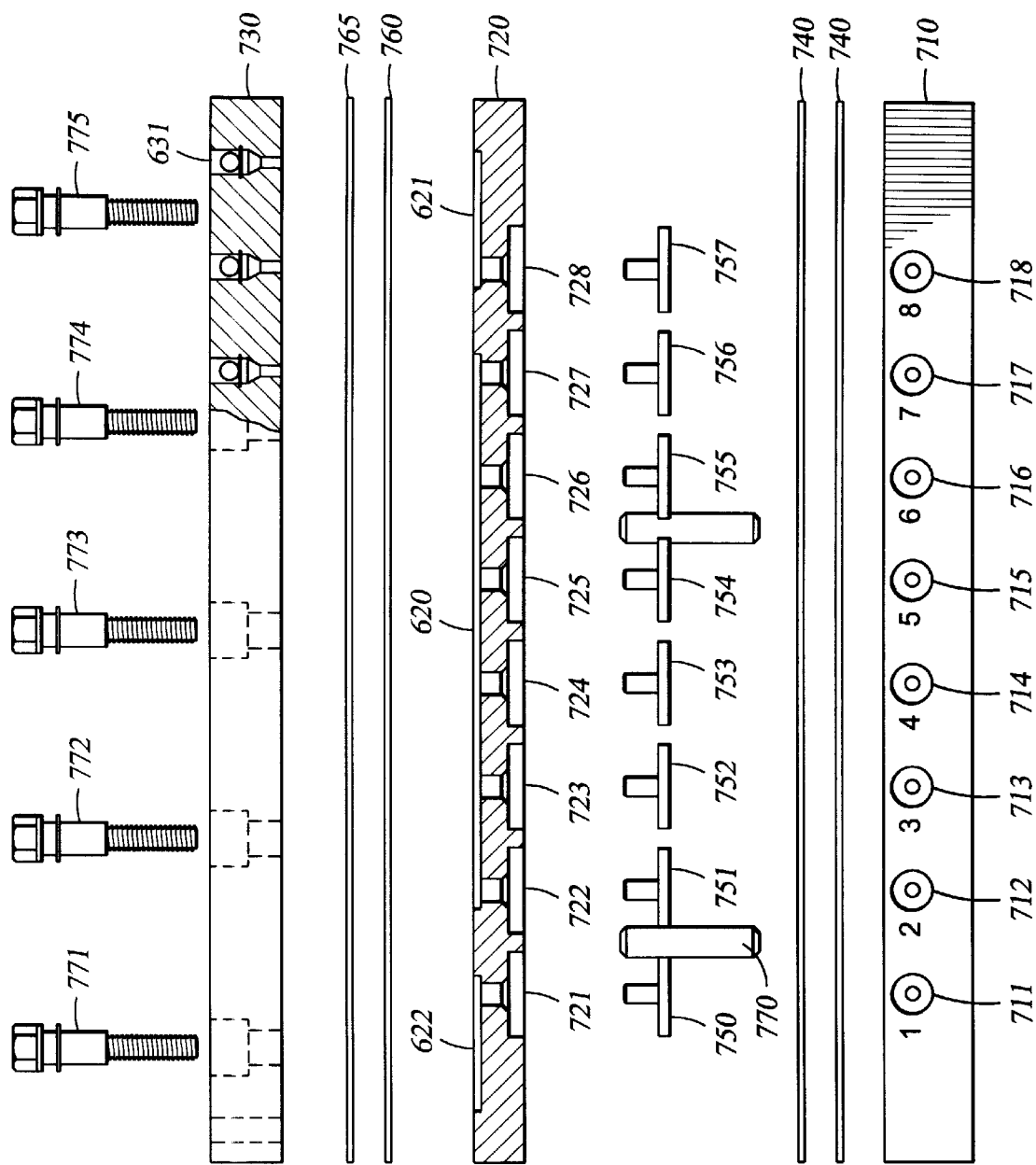
FIG. 7 is an exploded view of an earlier design of the stream switching system of FIG. 6.

A difference between the switching system of FIGS. 6 and 7 and that of FIG. 1 is the method of controlling sample fluid flow. Unlike the stream switching system of FIGS. 6 and 7, which uses an array of pistons and membranes to control sample fluid flow, the embodiment of FIGS. 1A and 1B directly controls the fluid flow through the solenoids. In other words, in the embodiment of FIGS. 6 and 7 the sample fluid never flows through the solenoids. In FIGS. 1A and 1B, the sample fluid flows through the solenoid, where it is halted or allowed to pass through.

One feature of this invention is the use of default-closed solenoids that, unlike typical solenoids, remain closed when electrical power is not supplied. Consequently, when solenoids are used to control the flow of sample fluid directly, as shown, and electrical power to the solenoids fails, the sample will not leak through the sample handling system 100. In previous systems, a leak at the solenoids resulted in a loss of actuation pressure, which allowed the sample to leak internally past the pistons.

To the inventors' knowledge, while default-closed solenoids are currently available for other applications, default-closed, low dead-volume solenoids have never before been used in the sample handling art. In fact, previous default-closed solenoids would not be suitable for a full range of sample handling applications because of the wider range of temperatures encountered in the field and the relatively high internal leakage rate of the solenoids. Preferably, the solenoids used with the invention are specially adapted Pneutronics SRS 3-way solenoids. The solenoids were selected for their minimal leakage rate (i.e. <0.016 Standard Cubic Centimeters per Minute or SCCM Helium) and temperature limit (i.e. 0 to 70 degrees Celsius). However, the operating range during pipeline analysis is more severe, and an operational temperature range of −18 to 55° C. is needed for full performance. To adapt these solenoids to the wide temperature ranges encountered in sample handling system, it is desirable to increase the voltage applied to the solenoids. It has been found that increasing the solenoid voltage from 12 to 13 ensures that 1-watt solenoids would switch reliably at lower temperatures. Otherwise, unacceptable levels of leakage through the solenoids will occur. Leakage results in the undesirable mixing of fluid samples.

One advantage to the embodiments of the invention as pictured herein is their capability to be used with the software of FIGS. 6 and 7. The stream switching system of FIGS. 6 and 7 has eight solenoids. The embodiment of FIG. 1A includes six solenoids. However, the solenoids labeled SV1, SV3–SV6, and SV8 in FIG. 1A correspond to the solenoids labeled SV1, SV3–SV6 and SV8 in FIGS. 6 and 7. This aspect of the invention allows "plug and play" replacement of the old stream switching system of FIGS. 6 and 7 with the novel system of FIGS. 1A and 1B.

Figure 2:
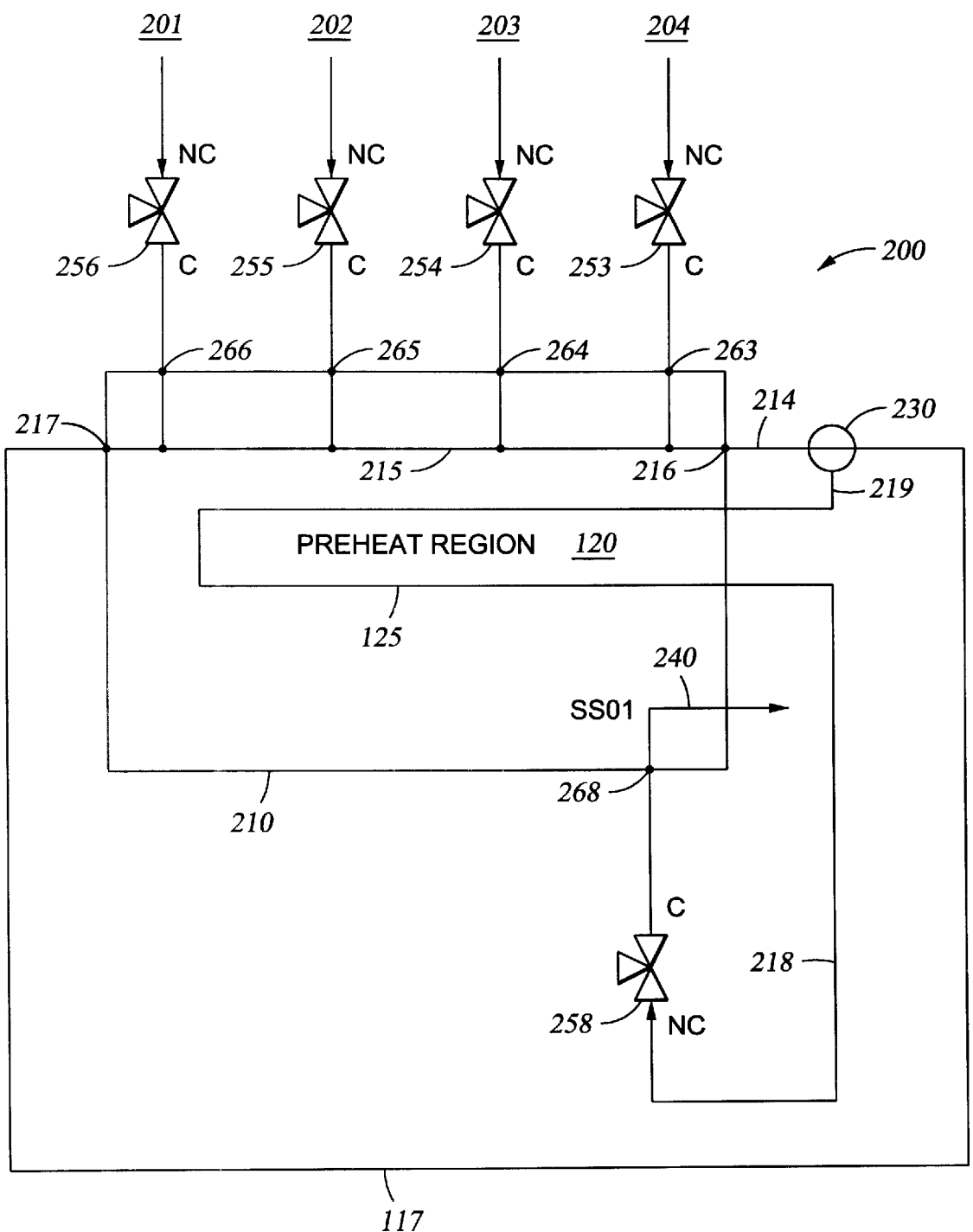
FIG. 2 is a schematic of a second embodiment of the invention.

FIG. 2 is an alternate embodiment of an inventive stream switching system. Stream switching system 200 includes a housing 210 with gas ports 263–266, 268. Housing 210 forms a common path channel 215 that exits one side of the housing 210 at location 216 and exits another side of the housing 210 at location 217. Tubing attaches to common path channel exits points 216 and 217 and meets at the union tee flow splitter 230. The union tee device is still referred to as a "splitter", despite being used to consolidate two flow paths into one in the embodiment of FIG. 2. Tubing from the union tee flow splitter 230 forms common path channel 219 that enters a pre-heat region 220, defined by housing 210. This tubing acts as a pre-heat coil while inserted in pre-heat region 220. An optional restrictor 225, in the pre-heat region, such as capillary tubing, may also be present if desired. A plurality of solenoids 253–256, 258 attach to ports 263–266, 268. Sample shut off channel one ("SS01") 240 attaches upstream to solenoid 258 via gas port 268. SS01 240 connects downstream to one or more gas chromatographs or sample valves (not shown).

Figure 3A:
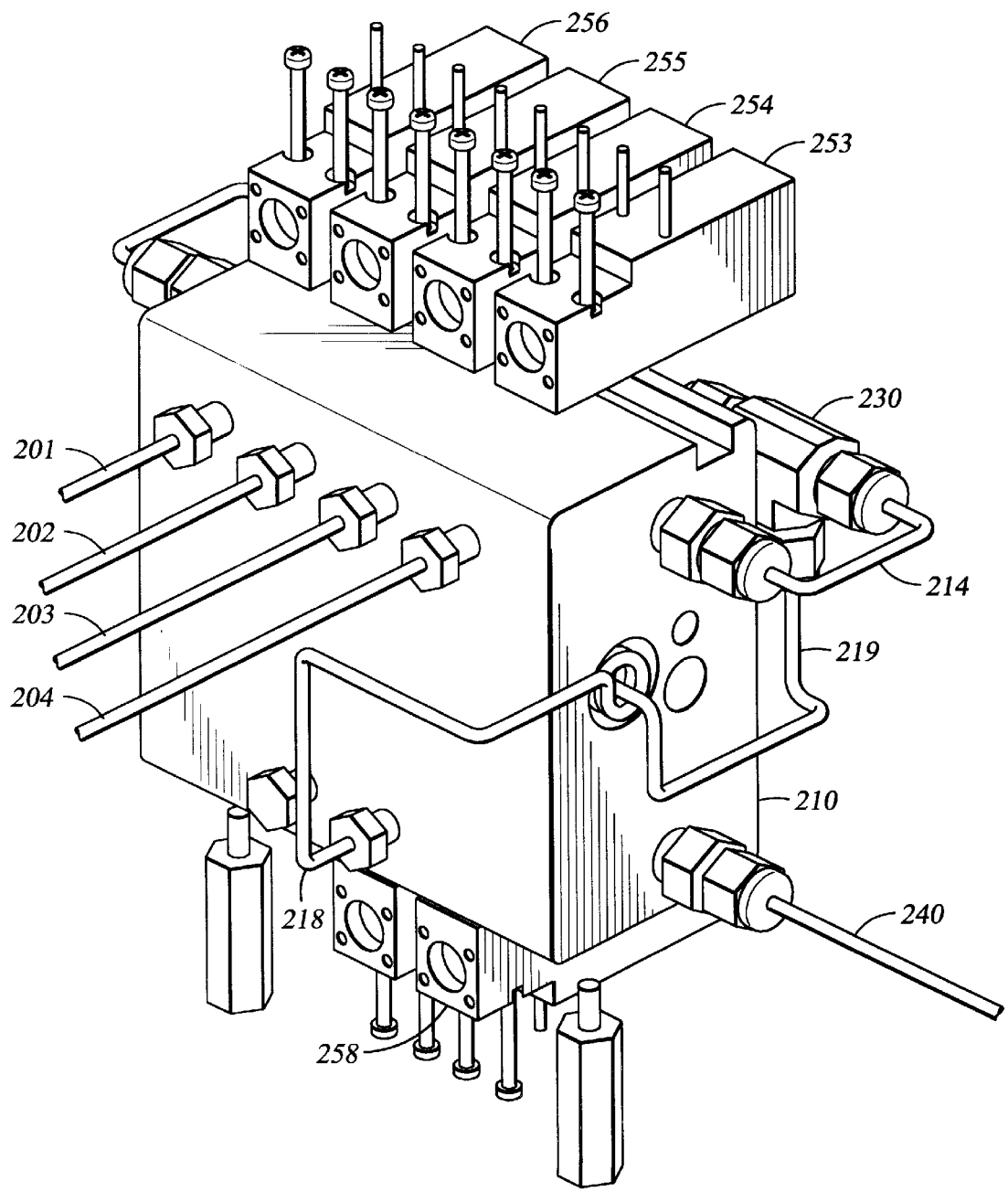
FIG. 3A is a first perspective view of the second embodiment of the invention.
Figure 3B:
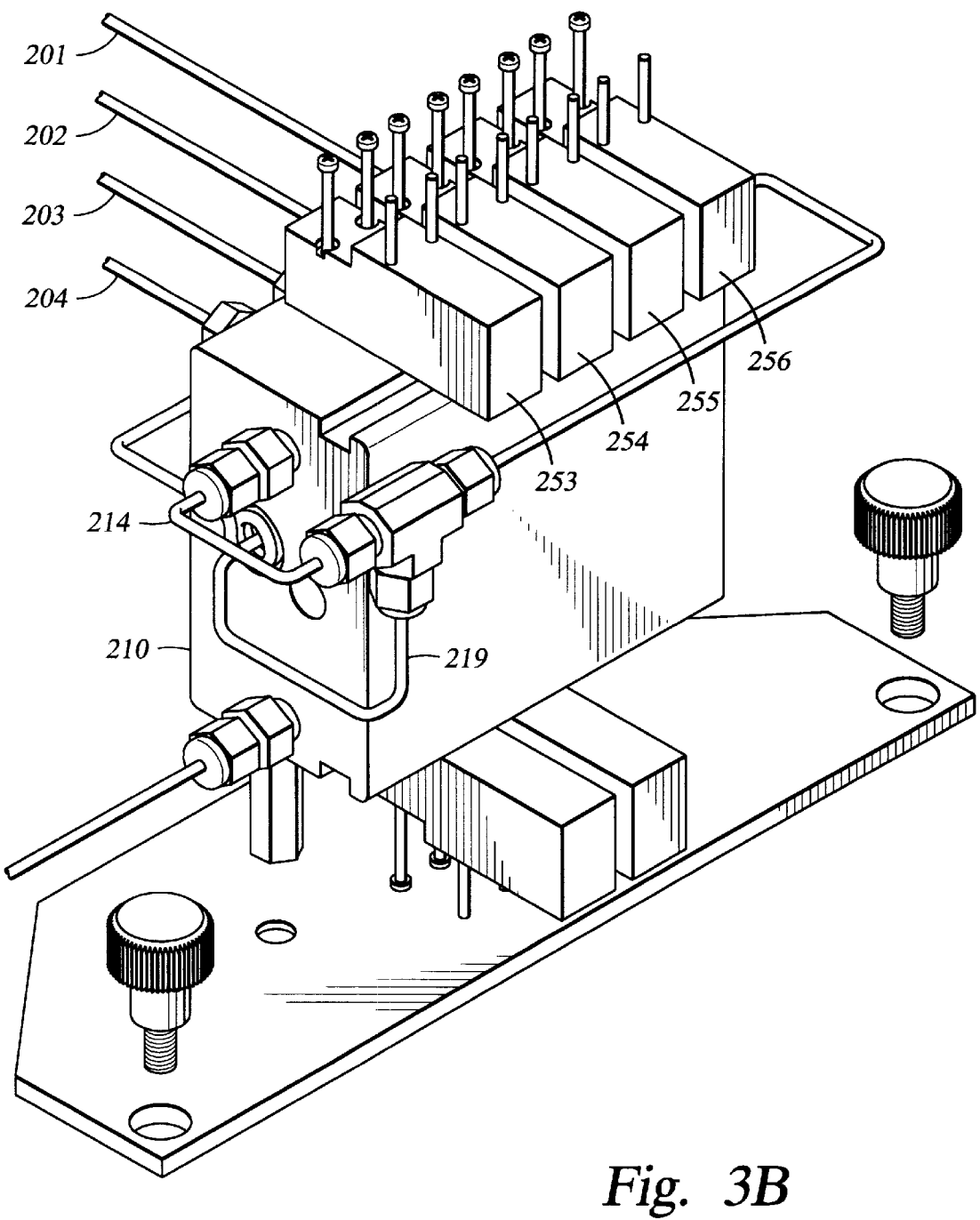
FIG. 3B is a second perspective view of the second embodiment of the invention.

FIGS. 3A and 3B are perspective views from the outside of the stream switching system of FIG. 2. FIG. 3B shows the system mounted horizontally. Referring to FIGS. 3A and 3B, solenoids 253–256 attach to stream switching housing 210. Tubing 214, comprising a part of the common stream channel, attaches on one end to housing 210 and on the other to the union tee flow splitter 230.

One difference between the embodiments of FIGS. 2, 3A and 3B and the previous embodiments of FIGS. 1A and 1B is the absence of plug 170 in the embodiment of FIGS. 2, 3A and 3B. Instead, tubing attached to the other end of the common stream portion 215 at exit port 217. This change, incorporated with the union tee flow splitter 230, improves sample purging of the common stream portion 215 and minimizes carryover between streams. This improves measurement accuracy.

Figure 4:
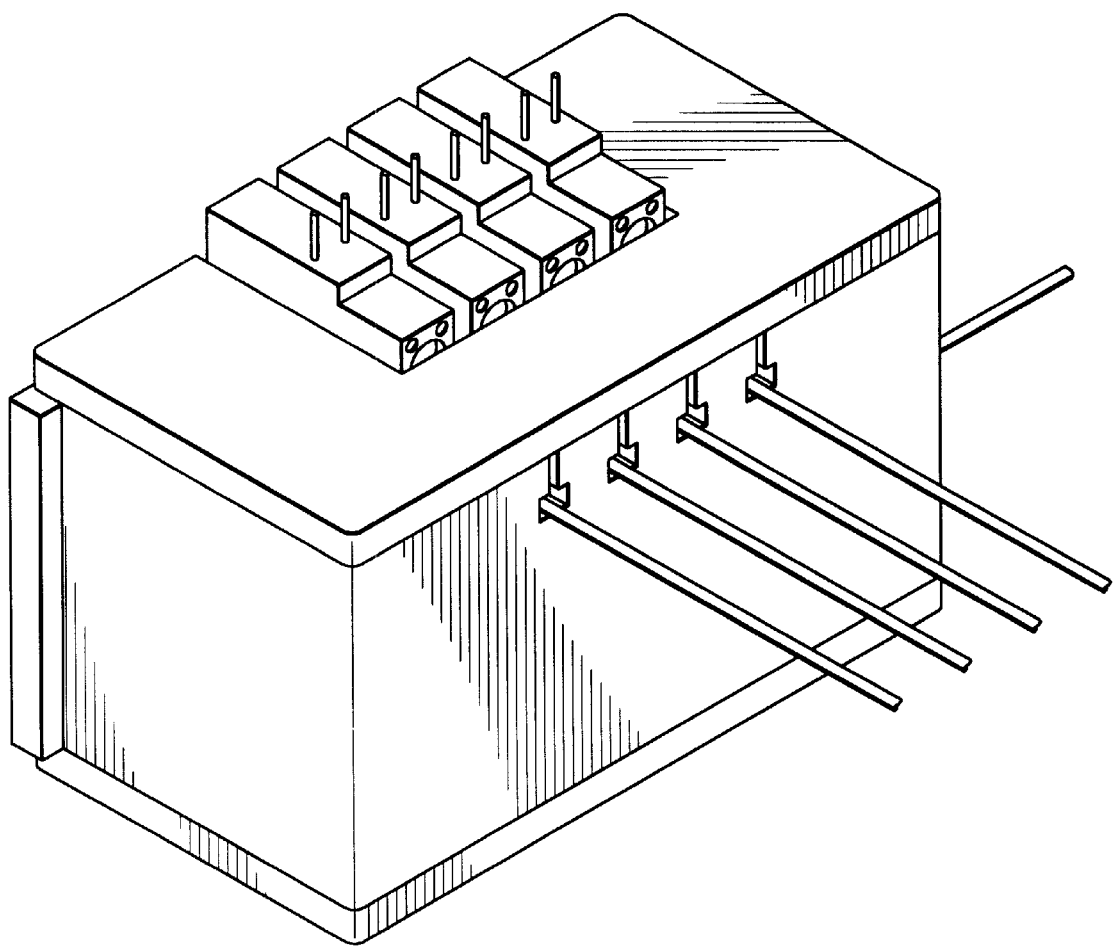
FIG. 4 is a diagram of a stream switching system according to the invention in an insulative oven.

FIGS. 3 and 4 illustrate the union tee flow splitter mounted against the housing 110 in an upright, horizontal position. All other factors being the same, a horizontal placement (i.e. the long portion or the top of the union tee being in the horizontal plane) of the flow splitter helps achieve a 50/50 flow from the lines leading into the union tee splitter to the common line. Tubing 219, comprising a different part of the common stream channel, leads from flow splitter 230 into the preheat region 220 of housing 210. There, the tubing coils (as shown) heat the sample to the desired temperature. From the pre-heat region 220 of the housing 210, the tubing leads to solenoid 258. SS01 tubing 240 leads from housing 210 to a downstream sample valve, gas chromatograph, or the like.

FIG. 4 shows the insulative oven in which the stream switching system is placed. The structure actually comprises three separate zones. An outside zone may range from 18° C. to 55° C. A first insulated zone contains the solenoids (or other switching elements), the stream switching system, and the heating element. The second insulated zone, interior to an additional layer of insulative material around the stream switching system, contains only the stream switching system and the heating element. Preferably, the insulation of the insulative oven comprises PORON BF1000 foam or equivalent.

Figure 5A:
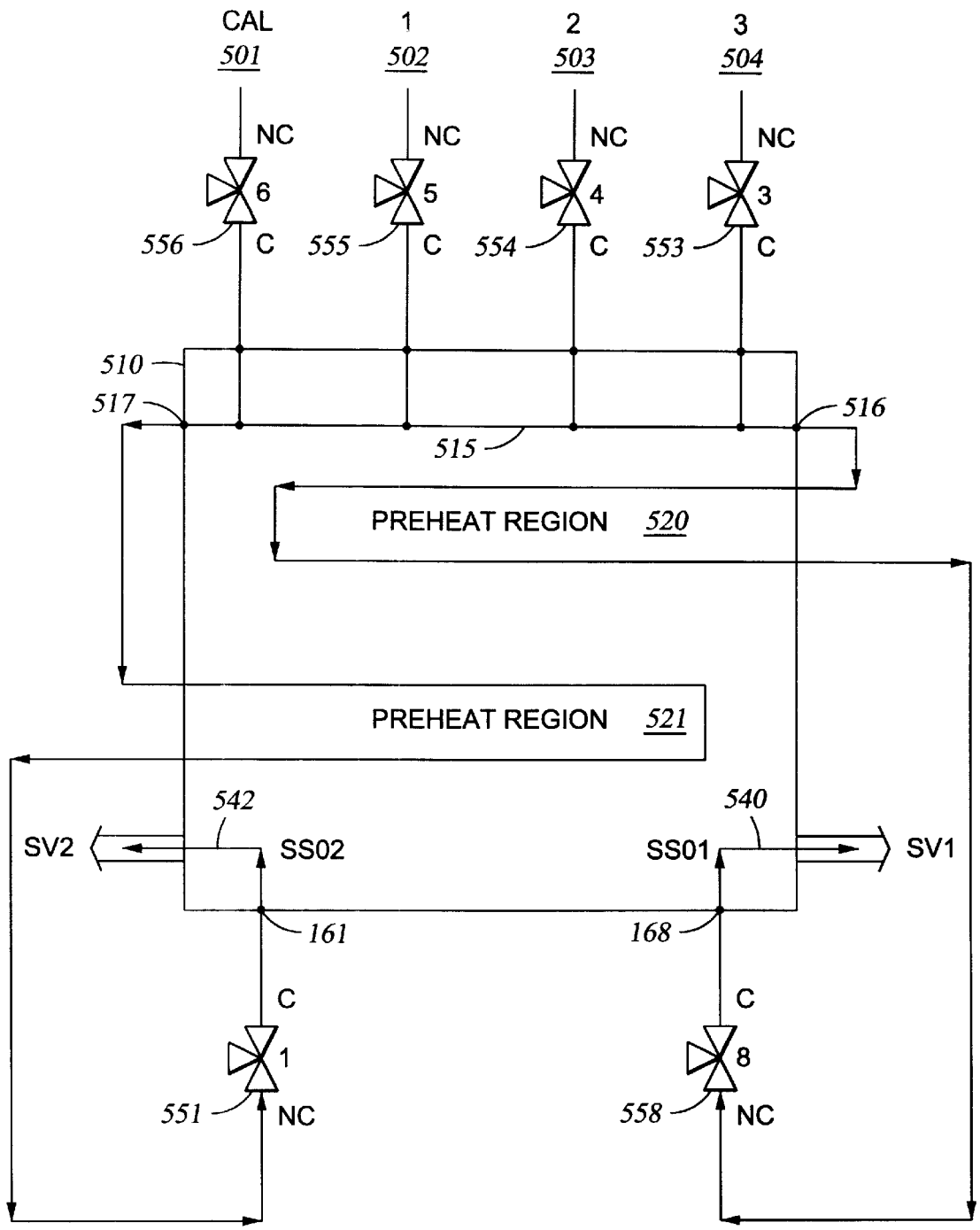
FIG. 5A is a schematic of a third embodiment of the invention.
Figure 5B:
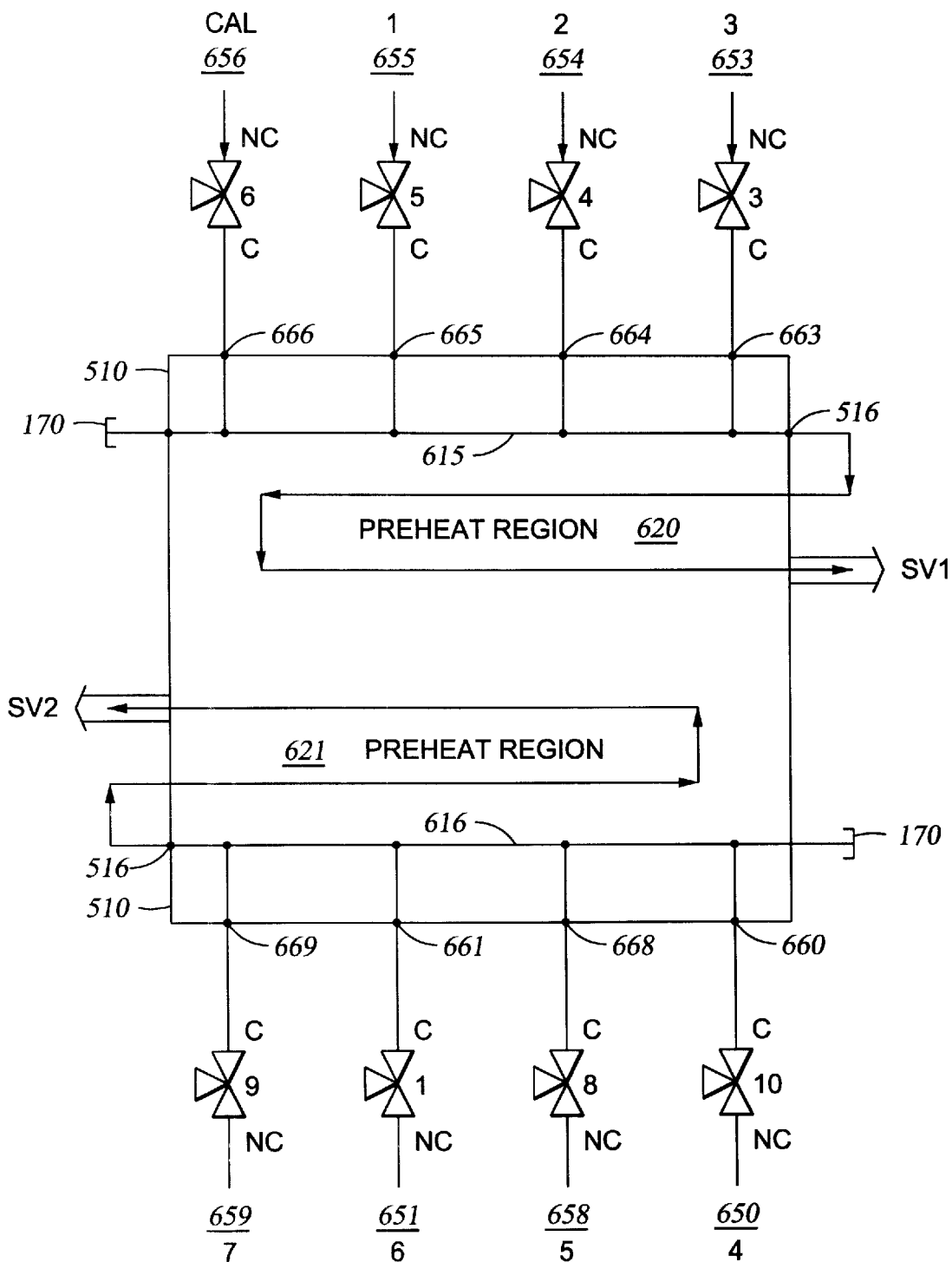
FIG. 5B is a schematic of a fourth embodiment of the invention.

Further alternate embodiments of the invention are shown in FIGS. 5A and 5B. Like the embodiments of FIGS. 1A, 1B, and 2, the embodiment of FIG. 5A is a double block design including six solenoids. Common stream path 515 exits housing 510 on two sides, at ports 516 and 517. Tubing connects to port 516 and travels through pre-heat region 520. This portion of the common stream path connects to solenoid 558. Solenoid 558 connects to first sample shut off channel 540. Attached TEFLON fluoropolymer film-sleeved tubing leads downstream to, e.g., sample valve 1. The TEFLON fluoropolymer film sleeve creates an air-gap around the tubing that minimizes heat-loss of the sample between the stream switching system and the sample valve. Tubing connects to port 517 and travels through a separate pre-heat region inside the housing 510, pre-heat region 521. This portion of the common stream path connects to solenoid 551. Solenoid 551 connects to second sample shut off 542. Attached TEFLON fluoropolymer film-covered tubing leads downstream to e.g., sample valve 2.

FIG. 5B illustrates a "single block" embodiment of the invention. A first common stream channel 615 includes ports 663, 664, 665, 666. Attached to these ports are solenoids 653, 654, 655, 656, respectively. Tubing attaches to first common stream channel 615 and travels through a heating channel in pre-heat region 620. This is attached downstream to sample valve 1. A second common stream channel 616 includes ports 660, 661, 668, 669. Attached to these ports are solenoids 650, 658, 651, 659, respectively. Tubing attaches to second common stream channel 616 and travels through a heating channel in pre-heat region 621. This is attached downstream to sample valve 2.

Because the embodiment of FIG. 5B is "single block", a total of eight streams (including two calibration streams) can be provided to the housing in a housing design that might otherwise accommodate only four. However, to avoid mixing among the streams, adequate sealing must be achieved by each of the solenoids. In addition, unlike the other embodiments described herein, the embodiment of FIG. 5B is not fully compatible with the software implemented for the system of FIGS. 6 and 7 (unless replacing a ten port stream switching system).

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. A stream switching system comprising:
    a housing having an exterior, said housing defining a common stream path, a first port, a second port, and a third port, wherein said first, second, and third ports each connect said common stream path to said exterior of said housing at different locations;
    a first flow switch connected on a first side to said first port and connected on a second side to a first fluid source, said first flow switch being actuatable between an open position that allows flow of fluid from said first fluid source through said first flow switch and a closed position that prevents the flow of fluid from said first fluid source, wherein said first switch is in either an open position or a closed position according to the application of electrical power, said first switch being in a closed position in the absence of electrical power applied to said first switch;
    a second flow switch connected on a first side to said second port and connected on a second side to a second fluid source, said second flow switch being actuatable between an open position that allows flow of fluid from said second fluid source through said second flow switch and a closed position that prevents the flow of fluid from said second fluid source, wherein said second switch is in either an open position or a closed position according to the application of electrical power, said second switch being in a closed position in the absence of electrical power applied to said second switch;
    a third flow switch connected on a first side to said third port and connected on a second side to a third fluid source, said third flow switch being actuatable between an open position that allows flow of fluid from said third fluid source through said third flow switch and a closed position that prevents the flow of fluid from said third fluid source, wherein said first switch is in either an open position or a closed position according to the application of electrical power, said third switch being in a closed position in the absence of electrical power applied to said third switch;
    a first sample shut off channel defined by said housing;
    a fourth port defined by said housing, said fourth port connecting said first sample shut off channel to said exterior of said housing;
    a fourth flow switch connected to said fourth port on a first side and to said common stream path on a second side, said fourth flow switch being actuatable between an open position that allows flow of fluid from said common stream path through said fourth flow switch and a closed position that prevents the flow of fluid from said common stream path, said fourth flow switch being in a closed position in the absence of electrical power;
    a heating channel defined by and inside said housing;
    tubing having a first end and a second end, said tubing being connected by said first end to said common stream path and by said second end to said fourth flow switch, said tubing traveling through said heating channel.

2. The stream switching system of claim 1, wherein said housing is a one-piece housing.

3. The stream switching system of claim 1, further comprising:
    a first sample shut off channel defined by said housing;
    a fourth port defined by said housing, said fourth port connecting said first sample shut off channel to said exterior of said housing;
    a fourth flow switch connected to said fourth port on a first side and to said common stream path on a second side, said fourth flow switch being actuatable between an open position that allows flow of fluid from said common stream path through said fourth flow switch and a closed position that prevents the flow of fluid from said first fluid source, said fourth flow switch being in a closed position in the absence of electrical power.

4. The stream switching system of claim 1, wherein said tubing includes a flow restrictor.

5. The stream switching system of claim 1, wherein said housing is formed from stainless steel.

6. The stream switching system of claim 1, wherein said first flow switch, said second flow switch, and said third flow switch are default-closed solenoids.

7. The stream switching system of claim 1, further comprising:
- a second common stream path defined by said housing, a fourth port, a fifth port, and a sixth port, wherein said fourth, fifth, and sixth ports each connect said second common stream path to said exterior of said housing at different locations;
- a fourth flow switch connected on a first side to said fourth port and connected on a second side to a fourth fluid source, said first flow switch being actuatable between an open position that allows flow of fluid from said fourth fluid source through said fourth flow switch and a closed position that prevents the flow of fluid from said fourth fluid source, wherein said fourth switch is in either an open position or a closed position according to the application of electrical power, said fourth switch being in a closed position in the absence of electrical power;
- a fifth flow switch connected on a first side to said fifth port and connected on a second side to a fifth fluid source, said fifth flow switch being actuatable between an open position that allows flow of fluid from said fifth fluid source through said fifth flow switch and a closed position that prevents the flow of fluid from said fifth fluid source, wherein said fifth switch is in either an open position or a closed position according to the application of electrical power, said fifth switch being in a closed position in the absence of electrical power applied to said fifth switch;
- a sixth flow switch connected on a first side to said sixth port and connected on a second side to a sixth fluid source, said sixth flow switch being actuatable between an open position that allows flow of fluid from said sixth fluid source through said sixth flow switch and a closed position that prevents the flow of fluid from said sixth fluid source, wherein said sixth switch is in either an open position or a closed position according to the application of electrical power, said sixth switch being in a closed position in the absence of electrical power applied to said sixth switch.

8. The stream switching system of claim 1, wherein said switches are solenoids operated at voltages adequate to ensure cold weather operation at −18 degrees Celsius.

9. A stream switching system comprising:
- a housing having an exterior, said housing defining a common stream path, a first port, a second port, and a third port, wherein said first, second, and third ports each connect said common stream path to said exterior of said housing at different locations;
- a first flow switch connected on a first side to said first port and connected on a second side to a first fluid source, said first flow switch being actuatable between an open position that allows flow of fluid from said first fluid source through said first flow switch and a closed position that prevents the flow of fluid from said first fluid source, wherein said first switch is in either an open position or a closed position according to the application of electrical power, said first switch being in a closed position in the absence of electrical power applied to said first switch;
- a second flow switch connected on a first side to said second port and connected on a second side to a second fluid source, said second flow switch being actuatable between an open position that allows flow of fluid from said second fluid source through said second flow switch and a closed position that prevents the flow of fluid from said second fluid source, wherein said second switch is in either an open position or a closed position according to the application of electrical power, said second switch being in a closed position in the absence of electrical power applied to said second switch;
- a third flow switch connected on a first side to said third port and connected on a second side to a third fluid source, said third flow switch being actuatable between an open position that allows flow of fluid from said third fluid source through said third flow switch and a closed position that prevents the flow of fluid from said third fluid source, wherein said first switch is in either an open position or a closed position according to the application of electrical power, said third switch being in a closed position in the absence of electrical power applied to said third switch;
- a first sample shut off channel defined by said housing;
- a second sample shut off channel defined by said housing;
- a fourth port defined by said housing, said fourth port connecting said first sample shut off channel to said exterior of said housing;
- a fifth port defined by said housing, said fifth port connecting said second sample shut off channel to said exterior of said housing;
- a fourth flow switch connected to said fourth port on a first side and to said common stream path on a second side, said fourth flow switch being actuatable between an open position that allows flow of fluid from said common stream path through said fourth flow switch and a closed position that prevents the flow of fluid from said first fluid source, said fourth flow switch being in a closed position in the absence of electrical power;
- a fifth flow switch connected to said fifth port on a first side and to said common stream path on a second side, said fourth flow switch being actuatable between an open position that allows flow of fluid from said common stream path through said fourth flow switch and a closed position that prevents the flow of fluid from said first fluid source, said fourth flow switch being in a closed position in the absence of electrical power; and
- a flow splitter connected to said common stream path, said second side of said fourth flow switch, and said second side of said fifth flow switch.

10. A stream switching system comprising:
- a housing having an exterior, said housing defining a common stream path, a first port, a second port, and a third port, wherein said first, second, and third ports each connect said common stream path to said exterior of said housing at different locations;
- a first flow switch connected on a first side to said first port and connected on a second side to a first fluid source, said first flow switch being actuatable between an open position that allows flow of fluid from said first fluid source through said first flow switch and a closed position that prevents the flow of fluid from said first fluid source, wherein said first switch is in either an open position or a closed position according to the application of electrical power, said first switch being in a closed position in the absence of electrical power applied to said first switch;
- a second flow switch connected on a first side to said second port and connected on a second side to a second fluid source, said second flow switch being actuatable between an open position that allows flow of fluid from said second fluid source through said second flow switch and a closed position that prevents the flow of fluid from said second fluid source, wherein said second switch is in either an open position or a closed position according to the application of electrical power, said second switch being in a closed position in the absence of electrical power applied to said second switch;

a third flow switch connected on a first side to said third port and connected on a second side to a third fluid source, said third flow switch being actuatable between an open position that allows flow of fluid from said third fluid source through said third flow switch and a closed position that prevents the flow of fluid from said third fluid source, wherein said first switch is in either an open position or a closed position according to the application of electrical power, said third switch being in a closed position in the absence of electrical power applied to said third switch, wherein said housing further defines a chamber for insertion of a heating element.

11. A stream switching system comprising:

a housing having an exterior, said housing defining a common stream path, a first port, a second port, and a third port, wherein said first, second, and third ports each connect said common stream path to said exterior of said housing at different locations;

a first flow switch connected on a first side to said first port and connected on a second side to a first fluid source, said first flow switch being actuatable between an open position that allows flow of fluid from said first fluid source through said first flow switch and a closed position that prevents the flow of fluid from said first fluid source, wherein said first switch is in either an open position or a closed position according to the application of electrical power, said first switch being in a closed position in the absence of electrical power applied to said first switch;

a second flow switch connected on a first side to said second port and connected on a second side to a second fluid source, said second flow switch being actuatable between an open position that allows flow of fluid from said second fluid source through said second flow switch and a closed position that prevents the flow of fluid from said second fluid source, wherein said second switch is in either an open position or a closed position according to the application of electrical power, said second switch being in a closed position in the absence of electrical power applied to said second switch;

a third flow switch connected on a first side to said third port and connected on a second side to a third fluid source, said third flow switch being actuatable between an open position that allows flow of fluid from said third fluid source through said third flow switch and a closed position that prevents the flow of fluid from said third fluid source, wherein said first switch is in either an open position or a closed position according to the application of electrical power, said third switch being in a closed position in the absence of electrical power applied to said third switch, wherein said housing further defines a chamber for insertion of a thermal detector.

12. A stream switching system comprising:

a housing having an exterior, said housing defining a common stream path, a first port, a second port, and a third port, wherein said first, second, and third ports each connect said common stream path to said exterior of said housing at different locations;

a first flow switch connected on a first side to said first port and connected on a second side to a first fluid source, said first flow switch being actuatable between an open position that allows flow of fluid from said first fluid source through said first flow switch and a closed position that prevents the flow of fluid from said first fluid source, wherein said first switch is in either an open position or a closed position according to the application of electrical power, said first switch being in a closed position in the absence of electrical power applied to said first switch;

a second flow switch connected on a first side to said second port and connected on a second side to a second fluid source, said second flow switch being actuatable between an open position that allows flow of fluid from said second fluid source through said second flow switch and a closed position that prevents the flow of fluid from said second, fluid source wherein said second switch is in either an open position or a closed position according to the application of electrical power, said second switch being in a closed position in the absence of electrical power applied to said second switch;

a third flow switch connected on a first side to said third port and connected on a second side to a third fluid source, said third flow switch being actuatable between an open position that allows flow of fluid from said third fluid source through said third flow switch and a closed position that prevents the flow of fluid from said third fluid source, wherein said first switch is in either an open position or a closed position according to the application of electrical power, said third switch being in a closed position in the absence of electrical power applied to said third switch, wherein said housing includes a heat dissipation channel proximate said first, second, and third flow switches.

13. A stream switching system comprising:

a housing having an exterior, said housing defining a common stream path, a first port, a second port, and a third port, wherein said first, second, and third ports each connect said common stream path to said exterior of said housing at different locations;

a first flow switch connected on a first side to said first port and connected on a second side to a first fluid source, said first flow switch being actuatable between an open position that allows flow of fluid from said first fluid source through said first flow switch and a closed position that prevents the flow of fluid from said first fluid source, wherein said first switch is in either an open position or a closed position according to the application of electrical power, said first switch being in a closed position in the absence of electrical power applied to said first switch;

a second flow switch connected on a first side to said second port and connected on a second side to a second fluid source, said second flow switch being actuatable between an open position that allows flow of fluid from said second fluid source through said second flow switch and a closed position that prevents the flow of fluid from said second fluid source, wherein said second switch is in either an open position or a closed position according to the application of electrical power, said second switch being in a closed position in the absence of electrical power applied to said second switch;

a third flow switch connected on a first side to said third port and connected on a second side to a third fluid source, said third flow switch being actuatable between an open position that allows flow of fluid from said third fluid source through said third flow switch and a closed position that prevents the flow of fluid from said third fluid source, wherein said first switch is in either an open position or a closed position according to the application of electrical power, said third switch being in a closed position in the absence of electrical power applied to said third switch;

a plug, wherein said common stream path includes a first end and a second end and wherein said second end of said common stream path terminates at said plug.

14. A stream switching system comprising:

a housing having an exterior, said housing defining a common stream path, a first port, a second port, and a third port, wherein said first, second, and third ports each connect said common stream path to said exterior of said housing at different locations;

a first flow switch connected on a first side to said first port and connected on a second side to a first fluid source, said first flow switch being actuatable between an open position that allows flow of fluid from said first fluid source through said first flow switch and a closed position that prevents the flow of fluid from said first fluid source, wherein said first switch is in either an open position or a closed position according to the application of electrical power, said first switch being in a closed position in the absence of electrical power applied to said first switch;

a second flow switch connected on a first side to said second port and connected on a second side to a second fluid source, said second flow switch being actuatable between an open position that allows flow of fluid from said second fluid source through said second flow switch and a closed position that prevents the flow of fluid from said second fluid source, wherein said second switch is in either an open position or a closed position according to the application of electrical power, said second switch being in a closed position in the absence of electrical power applied to said second switch;

a third flow switch connected on a first side to said third port and connected on a second side to a third fluid source, said third flow switch being actuatable between an open position that allows flow of fluid from said third fluid source through said third flow switch and a closed position that prevents the flow of fluid from said third fluid source, wherein said first switch is in either an open position or a closed position according to the application of electrical power, said third switch being in a closed position in the absence of electrical power applied to said third switch, a first sample shut off channel defined by said housing;

a fourth port defined by said housing, said fourth port connecting said first sample shut off channel to said exterior of said housing;

a fourth flow switch connected to said fourth port on a first side and to said common stream path on a second side, said fourth flow switch being actuatable between an open position that allows flow of fluid from said common stream path through said fourth flow switch and a closed position that prevents the flow of fluid from said first fluid source, said fourth flow switch being in a closed position in the absence of electrical power a flow splitter;

a first length of tubing connected to said common stream path at a first end of said common stream path;

a second length of tubing connected to said common stream path at a second end of said common stream path;

wherein said flow splitter connects to said first length of tubing, to said second length of tubing, and to said fourth flow switch.

15. A stream switching system comprising:

a housing having an exterior, said housing defining a common stream path, a first port, a second port, and a third port, wherein said first, second, and third ports each connect said common stream path to said exterior of said housing at different locations;

a first flow switch connected on a first side to said first port and connected on a second side to a first fluid source, said first flow switch being actuatable between an open position that allows flow of fluid from said first fluid source through said first flow switch and a closed position that prevents the flow of fluid from said first fluid source, wherein said first switch is in either an open position or a closed position according to the application of electrical power, said first switch being in a closed position in the absence of electrical power applied to said first switch;

a second flow switch connected on a first side to said second port and connected on a second side to a second fluid source, said second flow switch being actuatable between an open position that allows flow of fluid from said second fluid source through said second flow switch and a closed position that prevents the flow of fluid from said second fluid source, wherein said second switch is in either an open position or a closed position according to the application of electrical power, said second switch being in a closed position in the absence of electrical power applied to said second switch;

a third flow switch connected on a first side to said third port and connected on a second side to a third fluid source, said third flow switch being actuatable between an open position that allows flow of fluid from said third fluid source through said third flow switch and a closed position that prevents the flow of fluid from said third fluid source, wherein said first switch is in either an open position or a closed position according to the application of electrical power, said third switch being in a closed position in the absence of electrical power applied to said third switch;

a first sample shut off channel defined by said housing;

a second sample shut off channel defined by said housing;

a fourth port defined by said housing, said fourth port connecting said first sample shut off channel to said exterior of said housing;

a fifth port defined by said housing, said fifth port connecting said second sample shut off channel to said exterior of said housing;

a fourth flow switch connected to said fourth port on a first side and to a first end of said common stream path on a second side, said fourth flow switch being actuatable between an open position that allows flow of fluid from said common stream path through said fourth flow switch and a closed position that prevents the flow of fluid from said first fluid source, said fourth flow switch being in a closed position in the absence of electrical power;

a fifth flow switch connected to said fifth port on a first side and to a second end of said common stream path on a second side, said fourth flow switch being actuatable between an open position that allows flow of fluid from said common stream path through said fourth flow switch and a closed position that prevents the flow of fluid from said first fluid source, said fourth flow switch being in a closed position in the absence of electrical power;

a first length of tubing connected between said first end of said common stream path and said second side of said fourth flow switch; and a second length of tubing connected between said second end of said common stream path and said second side of said fifth flow switch.

* * * * *